(12) United States Patent
Bellare et al.

(10) Patent No.: US 7,635,725 B2
(45) Date of Patent: Dec. 22, 2009

(54) CROSSLINKED POLYMERS

(75) Inventors: Anuj Bellare, Brighton, MA (US); Thomas S. Thornhill, Dover, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 530 days.

(21) Appl. No.: 11/359,845

(22) Filed: Feb. 21, 2006

(65) Prior Publication Data

US 2007/0197679 A1    Aug. 23, 2007

(51) Int. Cl.
C08F 2/46     (2006.01)
A61F 2/00    (2006.01)
A61F 2/02    (2006.01)
A61F 2/30    (2006.01)

(52) U.S. Cl. .................... 522/161; 522/150; 522/157; 522/184; 522/189; 522/178; 523/115; 525/333.7; 623/23.58; 623/18.11; 623/22.21; 623/20.14; 623/22.11; 623/11.11

(58) Field of Classification Search .................. 522/150, 522/157, 161, 184, 189, 178; 523/115; 525/333.7; 623/18.11, 20.14, 22.11, 22.21, 23.58
See application file for complete search history.

(56) References Cited

U.S. PATENT DOCUMENTS

| 5,037,928 | A | 8/1991 | Li et al. |
|---|---|---|---|
| 6,245,276 | B1 | 6/2001 | McNulty et al. |
| 6,281,264 | B1 | 8/2001 | Salovey et al. |
| 2002/0107300 | A1 | 8/2002 | Saum et al. |
| 2004/0266902 | A1 | 12/2004 | Shen et al. |
| 2006/0004168 | A1 | 1/2006 | Greer et al. |

FOREIGN PATENT DOCUMENTS

EP    1 072 276 A1    1/2001

WO    WO 2005/074619 A2    8/2005

OTHER PUBLICATIONS

Kurtz et al., "Anistrophy and oxidative resistance of highly crosslinked UHMWPE after deformation processing by solid-state ram extrusion", Biomaterials, vol. 27, pp. 24-34, 2006.
Oral et al., "Characterization of irradiated blends of α-tocopherol and UHMWPE", Biomaterials, vol. 26, pp. 6657-6663, 2005.
Oral et al., "α-Tocopherol-doped irradiated UHMWPE for high fatique resistance and low wear", Biomaterials, vol. 25, 5515-5522, 2004.
Turell et al., A study of the nanostructure and tensile properties of ultra-high molecular weight polyethylene, Biomaterials, vol. 25, pp. 3389-3398, 2004.
Kurtz et al., "Advances in the processing, sterilization, and crosslinking of ultra-high molecular weight polyethylene for total join arthroplasty", Biomaterials, vol. 20, 1659-1688, 1999.
Muratoglu et al., Unified wear model for highly crosslinked ultrahigh molecular weight polyethylenes (UHMWPE), Biomaterials, vol. 20, pp. 1463-1470, 1999.
Wang et al., "Lubrication and wear of ultra-high molecular weight polyethylene in total joint placements", Triology International, vol. 31, Nos. 1-3, pp. 17-33, 1998.
Tretinnikov et al., "Surface crosslinking of polyethylene by electron beam irradiation in air", Polymer, vol. 39, No. 24, pp. 6115-6120, 1998.
Maxwell et al., "The effect of high pressure annealing on the molecular network in polyethylene", Polymer, vol. 37, No. 15, pp. 3293-3301, 1996.
D'Angelo et al. "The Effect of Pressure-Annealing on the Oxidation Resistance of Irradiated UHMWPE." Transactions, vol. 31, Paper No. 0663, Chicago, IL (2006).
Designation F2003-02, "Standard Practice for Accelerated Aging of Ultra-High Molecular Weight Polyethylene after Gamma Irradiation in Air," ASTM International, West Conshohocken, PA, www.astm.org (Feb. 2003).

*Primary Examiner*—Sanza L McClendon
(74) *Attorney, Agent, or Firm*—Fish & Richardson P.C.

(57) ABSTRACT

Highly crystalline, oxidation resistant crosslinked polymeric materials such as crosslinked ultrahigh molecular weight polyethylenes having high wear resistance, enhanced stiffness, enhanced tensile strength, a high level of fatigue and crack propagation resistance, and enhanced creep resistance can be manufactured by the new methods described herein.

39 Claims, 8 Drawing Sheets

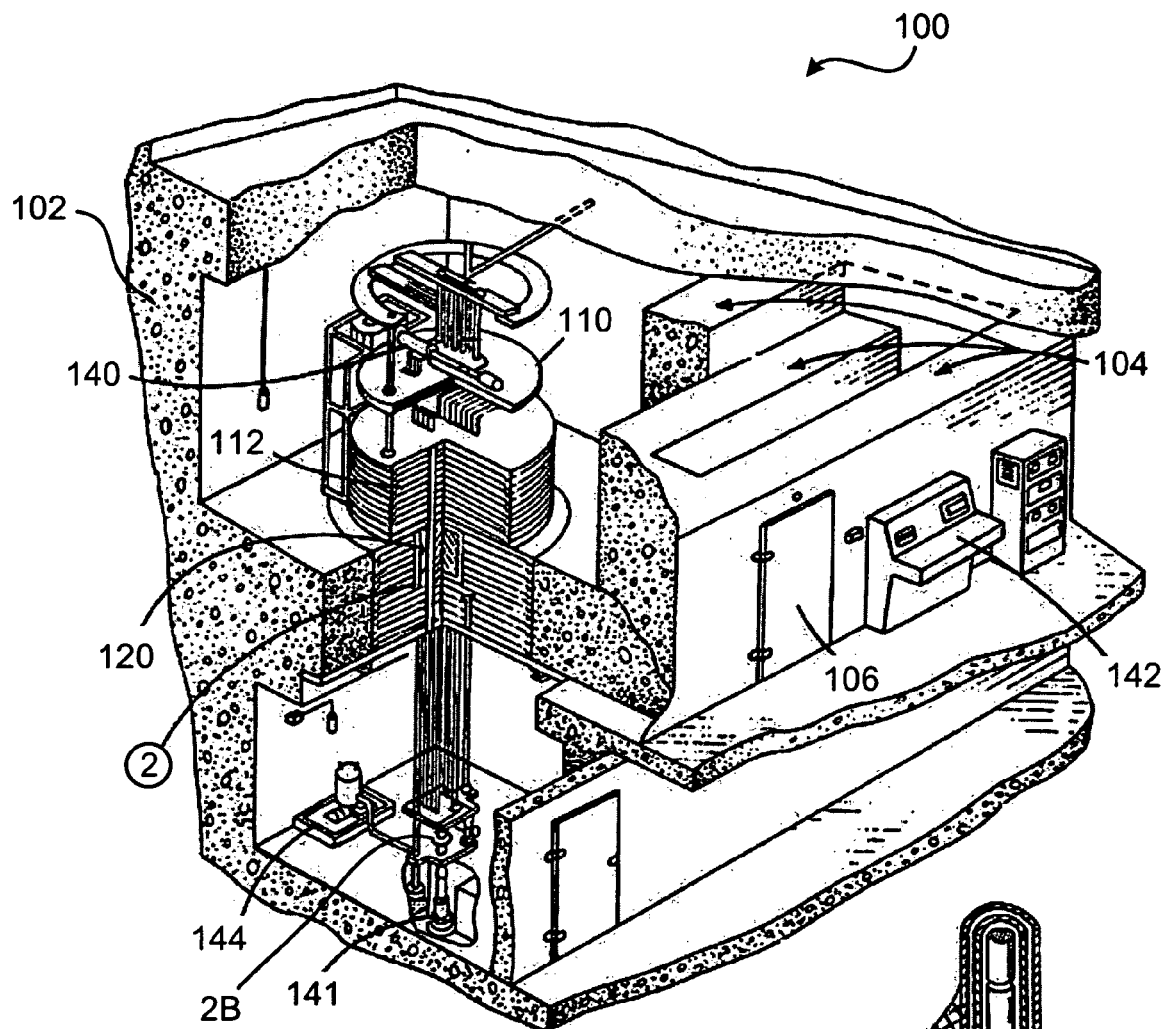
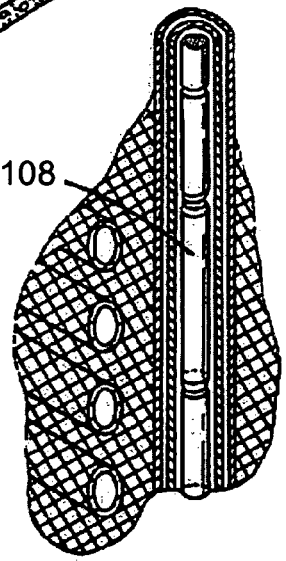
FIG. 1
FIG. 2

CROSSLINKED POLYMERS

TECHNICAL FIELD

This invention relates to crosslinked polymers, and to methods of making the same.

BACKGROUND

Polymeric materials are used in medical endoprostheses, e.g., orthopaedic implants (e.g., hip replacement prostheses). For example, ultrahigh molecular weight polyethylene (UHMWPE) is used to form components of artificial joints. Desirable characteristics for the polymeric materials used in medical endoprostheses include biocompatibility, a low coefficient of friction, a relatively high surface hardness, and resistance to wear and creep. It is also desirable for such endoprostheses to be readily sterilizable, e.g., by using high-energy radiation, or by utilizing a gaseous sterilant such as ethylene oxide, prior to implantation in a body, e.g., a human body.

High-energy radiation, e.g., in the form of gamma, x-ray, or electron beam radiation, is often a preferable method of sterilization for some endoprostheses because, in addition to sterilizing the endoprostheses, often the high energy radiation crosslinks the polymeric materials, thereby improving the wear resistance of the polymeric materials. However, while treatment of some endoprostheses with high-energy radiation can be beneficial, high-energy radiation can also have deleterious effects on some polymeric components. For example, treatment of polymeric components with high-energy radiation can result in the generation of long-lived, reactive species within the polymeric matrix, e.g., free radicals, radical cations, or reactive multiple bonds, that over time can react with oxygen, e.g., of the atmosphere or dissolved in biological fluids, to produce oxidative degradation in the polymeric materials.

Such degradation can reduce the wear resistance of the polymeric material. Therefore, it is often advantageous to reduce the number of such reactive species. Radiation sterilization of polymeric materials, crosslinking, and entrapment of long-lived, reactive species, and their relationship to wear are discussed in Kurtz et al., *Biomaterials*, 20, 1659-1688 (1999); Tretinnikov et al., *Polymer*, 39(4), 6115-6120 (1998); Maxwell et al., *Polymer*, 37(15), 3293-3301(1996); Kurtz et al., *Biomaterials*, 27, 24-34 (2006); Wang et al., *Tribology International*, 31(1-3), 17-33 (1998); Oral et al., *Biomaterials*, 26, 6657-6663 (2005); Oral et al., *Biomaterials*, 25, 5515-5522 (2004); Muratoglu et al., *Biomaterials*, 20, 1463-1470 (1999); Hamilton et al., European Patent Application No. 1072276A1; Li et al., U.S. Pat. No. 5,037,928, NcNulty et al., U.S. Pat. No. 6,245,276; and Muratoglu et al., PCT Publication No. WO 2005/074619.

SUMMARY

The invention is based, in part, on the discovery that maintaining or reducing a first degree of crystallinity of a substantially non-crosslinked polymeric material prior to crosslinking, followed by crosslinking the substantially non-crosslinked polymeric material to provide a crosslinked polymeric material, and then applying pressure to the crosslinked polymeric material, while heating the crosslinked material below a melting point of the crosslinked polymeric yields highly crystalline, oxidation resistant crosslinked polymeric materials. For example, crosslinked ultra-high molecular weight polyethylene (UHMWPE) having a degree of crystallinity greater than about 52 percent, and a melting point of greater than about 141° C. can be prepared using the methods described herein.

In one aspect, the invention features methods of making oxidation resistant crosslinked polymeric materials. The methods include obtaining a substantially non-crosslinked polymeric material having a first degree of crystallinity; maintaining or reducing the first degree of crystallinity of the substantially non-crosslinked polymeric material; crosslinking the substantially non-crosslinked polymeric material, to provide a crosslinked polymeric material; and then applying a pressure of greater than 10 MPa to the crosslinked polymeric material, while heating the crosslinked material below a melting point of the crosslinked polymeric material at the applied pressure for a time sufficient to provide the desired oxidation resistant, crosslinked polymeric material.

In some embodiments, the methods can further include, prior to crosslinking, heating the substantially non-crosslinked polymeric material having the first degree of crystallinity above a melting point of the substantially non-crosslinked polymeric material. For example, the methods can further include, prior to crosslinking, heating the substantially non-crosslinked polymeric material having the first degree of crystallinity above a melting point of the substantially non-crosslinked polymeric material, and then cooling the substantially non-crosslinked polymeric material with a fluid having a temperature below about 0° C. The substantially non-crosslinked polymeric material, can be, e.g., an olefin or a mixture of olefins, e.g., UHMWPE. For example, in a particular embodiment, the substantially non-crosslinked polymeric material is UHMWPE and the first degree of crystallinity is between about 50 and about 55 percent. A degree of crystallinity of the UHMWPE after heating above the melting point of the UHMWPE, and then cooling the melted UHMWPE to about 25° C. is between about 32 percent and about 48 percent.

In certain embodiments, the non-crosslinked polymeric material is substantially-free of biologically leachable additives. Leachable additives can, e.g., interfere with crosslinking, and can, e.g., have deleterious effects on animals, e.g., humans.

In some embodiments, the substantially non-crosslinked polymeric material, e.g., in the form of a cylindrical rod, includes UHMWPE. In other embodiments, the substantially non-crosslinked polymeric material includes a melt processible polymer or a blend of melt processible polymers.

In some embodiments, the crosslinking step includes irradiating the substantially non-crosslinked polymeric material with an ionizing radiation, e.g., in the form of gamma radiation, e.g., at a total dose of greater than 1 Mrad, and at an applied dose rate of greater than 0.1 Mrad/hour. The crosslinking can occur below a melting point of the substantially non-crosslinked polymeric material, or at temperatures above a melting point of the substantially non-crosslinked polymeric material. Crosslinking can occur, e.g., at nominal atmospheric pressure.

In some embodiments, prior to the application of any pressure above nominal atmospheric pressure, the crosslinked polymeric material is heated to a temperature that is between about 25° C. to about 0.5° C. below a melting point of the crosslinked polymeric material.

In certain embodiments, applying pressure while heating includes applying a pressure of above about 250 MPa at a temperature of between about 100° C. to about 1° C. below a melting point of the crosslinked polymeric material at the applied pressure, and then further heating above the temperature, but below a melting point of the crosslinked polymeric material. Pressure can be applied, e.g., along a single axis.

In another aspect, the invention features medical endoprostheses, or a portion thereof, that include the oxidation resistant crosslinked polymeric materials described herein.

In another aspect, the invention features a crosslinked UHMWPE having a melting point greater than about 141° C., and a degree of crystallinity of greater than about 52 percent, e.g., greater than about 56 percent. In some embodiments, the crosslinked UHMWPE has a crosslink density of greater than about 100 mol/m$^3$, and/or a molecular weight between crosslinks of less than about 9,000 g/mol.

In another aspect, the invention features preforms, e.g., cylindrical slugs, made from the oxidation resistant crosslinked polymeric materials described herein.

In another aspect, the invention features methods of making oxidation resistant preforms. The methods include obtaining a preform that includes a substantially non-crosslinked polymeric material having a first degree of crystallinity; maintaining or reducing the first degree of crystallinity of the substantially non-crosslinked polymeric material; crosslinking the substantially non-crosslinked polymeric material, to provide a preform that includes a crosslinked polymeric material; and then applying a pressure of greater than 10 MPa to the preform that includes the crosslinked polymeric material, while heating the crosslinked material below a melting point of the crosslinked polymeric material at the applied pressure for a time sufficient to provide an oxidation resistant preform.

In some embodiments, the substantially non-crosslinked polymeric material is in the form of a cylindrical rod. The preform can be made by extrusion, e.g., thermoplastic extrusion or ram extrusion, or by molding, e.g., injection or compression molding.

Advantages include any one of, or combinations of, the following. The oxidation resistant crosslinked polymeric material is highly crystalline, e.g., having a crystallinity of greater than 54 percent, e.g., 57 percent or higher. The oxidation resistant crosslinked polymeric material is highly crosslinked, e.g., having a high crosslink density, e.g., greater than 100 mol/m$^3$, and/or a relatively low molecular weight between crosslinks, e.g., less than 9000 g/mol. When the oxidation resistant crosslinked polymeric material is UHMWPE, it can have a relatively high melting point, e.g., greater than 140° C., in combination with a relatively high degree of crystallinity, e.g., greater than about 52 percent. Parts formed from the oxidation resistant crosslinked polymeric material have high wear resistance, enhanced stiffness, as reflected in flexural and tensile moduli, a high level of fatigue and crack propagation resistance, and enhanced creep resistance. Some of the oxidation resistant crosslinked polymeric materials have a low coefficient of friction. The described methods are easy to implement.

An "oxidation resistant crosslinked polymeric material" is one that loses less than 25 percent of its elongation at break (ASTM D412, Die C, 2 hours, and 23° C.) after treatment in a bomb reactor filled with substantially pure oxygen gas to a pressure of 5 atmospheres, heated to 70° C. temperature, and held at this temperature for a period of two weeks.

A "substantially non-crosslinked polymeric material" is one that is melt processible, or in the alternative, dissolves in a solvent.

A "polymeric material that is substantially free of biologically leachable additives" is one that releases less than 0.01 weight percent when 1.0 gram of the test material is completely immersed in 100 mL of Ringer's solution at 25° C. for 24 hours. For the purposes of this disclosure, Ringer's solution is a solution of boiled distilled water containing 8.6 gram sodium chloride, 0.3 gram potassium chloride, and 0.33 gram calcium chloride per liter.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a perspective, cut-away view of a gamma irradiator.

FIG. 2 is an enlarged perspective view of region 2 of FIG. 1.

Like reference symbols in the various drawings indicate like elements.

DETAILED DESCRIPTION

Figure 3:
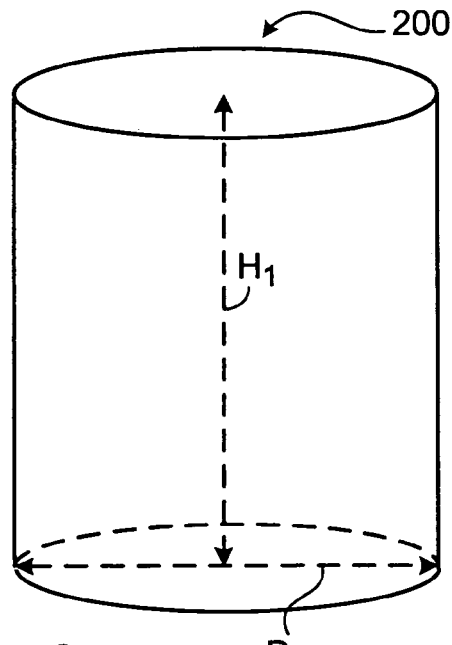
FIG. 3 is a schematic perspective view of a cylindrical plug cut from an extruded rod made from substantially non-crosslinked ultrahigh molecular weight polyethylene (UHMWPE).

The invention is based, in part, on the discovery that maintaining or reducing a first degree of crystallinity of a substantially non-crosslinked polymeric material prior to crosslinking, followed by crosslinking, e.g., by using ionizing radiation, the substantially non-crosslinked polymeric material to provide a crosslinked polymeric material, and then applying pressure, e.g., of greater than 250 MPa, to the crosslinked polymeric material, while heating the crosslinked material below a melting point of the crosslinked polymeric yields highly crystalline, oxidation resistant crosslinked polymeric materials.

General Methodology

Generally, highly crystalline and wear resistant oxidation resistant crosslinked polymeric materials can be prepared by first obtaining a substantially non-crosslinked polymeric material, e.g., a polyolefin such as an ultrahigh molecular weight polyethylene (UHMWPE), having a first degree of crystallinity. The first degree of crystallinity of the substantially non-crosslinked polymeric material is maintained or reduced, e.g., by maintaining the material substantially below its melting point, or by heating the material above a melting point of the substantially non-crosslinked polymeric material when it is desired to reduce crystallinity. The substantially non-crosslinked polymeric material is then crosslinked, e.g., by irradiating with an ionizing radiation such as gamma rays, or by heating the substantially non-crosslinked material together with radical source such as an azo compound, a peroxide, or a persulfate, to provide a crosslinked polymeric material.

After crosslinking, reactive species trapped within the polymeric matrix that can cause oxidation, e.g., free radicals, radical cations, or reactive multiple bonds, are removed, e.g., quenched, by applying a pressure of greater than 10 MPa to the crosslinked polymeric material, while heating the crosslinked material below a melting point of the crosslinked polymeric material at the applied pressure. In addition to reducing reactive species trapped in the polymeric matrix that can react with oxygen, the high pressure treatment can, e.g., improve the crystallinity of the crosslinked polymeric material. It is believed that the above-mentioned steps, and ordering of the steps produces crosslinked polymeric materials that are highly resistant to oxidation, have high crystallinities, high melting points, and exceptional mechanical properties. Parts, e.g., medical endoprostheses, or portions of medical endoprostheses, formed from the oxidation resistant crosslinked polymeric materials have high wear resistance, enhanced stiffness, a high level of fatigue and crack propagation resistance, and enhanced creep resistance.

Polymeric Materials

The substantially non-crosslinked polymeric material can be, e.g., a polyolefin, e.g., a polyethylene such as UHMWPE, a low density polyethylene (e.g., having a density of between about 0.92 and 0.93 g/cm$^3$, as determined by ASTM D792), a linear low density polyethylene, a very-low density polyethylene, an ultra-low density polyethylene (e.g., having a density of between about 0.90 and 0.92 g/cm$^3$, as determined by ASTM D792), a high density polyethylene (e.g., having a density of between about 0.95 and 0.97 g/cm$^3$, as determined by ASTM D792), or a polypropylene, a polyester such as polyethylene terephthalate, a polyamide such as nylon 6, 6/12, or 6/10, a polyethyleneimine, an elastomeric styrenic copolymer such as styrene-ethylene-butylene-styrene copolymer, or a copolymer of styrene and a diene such as butadiene or isoprene, a polyamide elastomer such as a polyether-polyamide copolymer, an ethylene-vinyl acetate copolymer, or compatible blends of any of these polymers. The substantially non-crosslinked polymeric material can be processed in the melt into a desired shape, e.g., using a melt extruder, or an injection molding machine, or it can be pressure processed with or without heat, e.g., using compression molding or ram extrusion.

The substantially non-crosslinked polymeric material can be purchased in various forms, e.g., as powder, flakes, particles, pellets, or other shapes such as rod (e.g., cylindrical rod). Powder, flakes, particles, or pellets can be shaped into a preform by extrusion, e.g., ram extrusion, melt extrusion, or by molding, e.g., injection or compression molding. Purchased shapes can be machined, cut, or other worked to provide the desired shape. Polyolefins are available, e.g., from Hoechst, Montel, Sunoco, Exxon, and Dow; polyesters are available from BASF and DuPont; nylons are available from DuPont and Atofina, and elastomeric styrenic copolymers are available from the KRATON Polymers Group (formally available from Shell). If desired, the materials may be synthesized by known methods. For example, the polyolefins can be synthesized by employing Ziegler-Natta heterogeneous metal catalysts, or metallocene catalyst systems, and nylons can be prepared by condensation, e.g., using transesterification.

In some embodiments, it is desirable for the substantially non-crosslinked polymeric material to be substantially free of biologically leachable additives that could leach from an implant in a human body or that could interfere with the crosslinking of the substantially non-crosslinked polymeric material.

In particular embodiments, the polyolefin is UHMWPE. For the purposes of this disclosure, an ultrahigh molecular weight polyethylene is a material that consists essentially of substantially linear, non-branched polymeric chains consisting essentially of —$CH_2CH_2$— repeat units. The polyethylene has an average molecular weight in excess of about 500,000, e.g., greater than 1,000,000, 2,500,000, 5,000,000, or even greater than 7,500,000, as determined using a universal calibration curve. In such embodiments, the UHMWPE can have a degree of crystallinity of greater than 50 percent, e.g., greater than 51 percent, 52 percent, 53 percent, 54 percent, or even greater than 55 percent, and can have a melting point of greater than 135° C., e.g., greater than 136, 137, 138, 139 or even greater than 140° C. Degree of crystallinity of the UHMWPE is calculated by knowing the mass of the sample (in grams), the heat absorbed by the sample in melting (E in J/g), and the heat of melting of polyethylene crystals ($\Delta H$=291 J/g). Once these quantities are known, degree of crystallinity is then calculated using the formula below:

$$\text{Degree of Crystallinity} = E/(\text{sample weight}) \cdot \Delta H.$$

For example, differential scanning calorimetry (DSC) can be used to measure the degree of crystallinity of the UHMWPE sample. To do so, the sample is weighed to a precision of about 0.01 milligrams, and then the sample is placed in an aluminum DSC sample pan. The pan holding the sample is then placed in a differential scanning calorimeter, e.g., a TA Instruments Q-1000 DSC, and the sample and reference are heated at a heating rate of about 10° C./minute from about −20° C. to 180° C., cooled to about −10° C., and then subjected to another heating cycle from about −20° C. to 180° C. at 10° C./minute. Heat flow as a function of time and temperature is recorded during each cycle. Degree of crystallinity is determined by integrating the enthalpy peak from 20° C. to 160° C., and then normalizing it with the enthalpy of melting of 100 percent crystalline polyethylene (291 J/g). Melting points can also be determined using DSC.

Maintaining or Reducing Crystallinity

After obtaining the substantially non-crosslinked polymeric material having a first degree of crystallinity, the first degree of crystallinity of the substantially non-crosslinked polymeric material is maintained or reduced. Crystallinity of the substantially non-crosslinked polymeric material can be decreased, e.g., by heating the substantially non-crosslinked polymeric material having a first degree of crystallinity to a temperature sufficient to decrease its degree of crystallinity. For example, the substantially non-crosslinked polymeric material can be heated to about its melting point, or to at least one of its melting points in the case of polymer blends, or to a temperature above its melt point, or at least one of its melting points. It is believed that such a heating regimen reduces the degree of crystallinity in the substantially non-crosslinked polymeric material, which can, e.g., allow for a greater degree of freedom of polymeric chains during crosslinking, and can provide fewer crystalline regions in which to trap reactive species. This can result in an increase in crosslink density and a reduction in molecular weight between crosslinks. Advantageously, higher crosslink densities can result in higher wear resistance. The structure of UHMWPE is discussed in Turell et al., *Biomaterials,* 25, 3389-3398 (2004).

After heating, the substantially non-crosslinked polymeric material is cooled to "freeze" the substantially non-crosslinked polymeric material at the desired degree of crystallinity. During cooling, cooling rates can be rather slow, e.g., from about 1° C. per minute to about 25° C. per minute, e.g., from about 2° C. per minute to about 10° C. per minute. Higher cooling rates can also be achieved. For example, after heating the substantially non-crosslinked polymeric material, cooling can be accomplished by contacting, e.g., by submerging, the substantially non-crosslinked polymeric material with a fluid having a temperature below about 0° C., e.g., liquid nitrogen with a boiling point of about 77 K. This can allow for rapid cooling rates, especially of skin portions of the substantially non-crosslinked polymeric. In such cases, cooling rates can be, e.g., from about 50° C. per minute to about 500° C. per minute, e.g., from about 100° C. to about 250° C. per minute. Rapid cooling rates can result in more nucleation sites, smaller crystallites, and a material having a higher surface area.

As an illustrative example, when UHMWPE is the substantially non-crosslinked polymeric material, it can have, e.g., a first degree of crystallinity of between about 50 and about 55 percent. After melting, the UHMWPE and cooling the melted UHMWPE to about 25° C., the crystallinity is reduced, e.g., to between about 32 percent and about 48 percent.

Crosslinking

After maintaining or reducing the first degree of crystallinity of the substantially non-crosslinked polymeric material, the substantially non-crosslinked polymeric material is crosslinked to provide crosslinked material.

In some embodiments, the crosslinking occurs at a temperature from about −25° C. to above a melting point of the substantially non-crosslinked polymeric material, e.g., from about −10° C. to about a melting point of the substantially non-crosslinked polymeric material, e.g., room temperature to about the melting point. Irradiating above a melting point of the substantially non-crosslinked polymeric material can, e.g., increase crosslink density.

In some embodiments, the crosslinking occurs at a pressure, e.g., from about nominal atmospheric pressure to about 50 atmospheres of pressure, e.g., from about nominal atmospheric pressure to about 5 atmospheres of pressure. Crosslinking above atmospheric pressure can, e.g., increase crosslink density.

In some embodiments, an ionizing radiation (e.g., an electron beam, x-ray radiation or gamma radiation) is employed to crosslink the substantially non-crosslinked polymeric material. In specific embodiments, gamma radiation is employed to crosslink the substantially non-crosslinked polymeric material. Referring to FIGS. 1 and 2, a gamma irradiator 100 includes gamma radiation sources 108, e.g., $^{60}$Co pellets, a working table 110 for holding the substantially non-crosslinked polymeric material to be irradiated, and storage 112, e.g., made of a plurality iron plates, all of which are housed in a concrete containment chamber 102 that includes a maze entranceway 104 beyond a lead-lined door 106. Storage 112 includes a plurality of channels 120, e.g., 16 or more channels, allowing the gamma radiation sources 108 to pass through storage 112 on their way proximate the working table 110.

In operation, the substantially non-crosslinked polymeric material to be irradiated is placed on working table 110. The irradiator is configured to deliver the desired dose rate and monitoring equipment is connected to experimental block 140. The operator then leaves the containment chamber 102, passing through the maze entranceway 104 and through the lead-lined door 106. The operator uses a control panel 142 to instruct a computer to lift the radiation sources 108 into working position using cylinder 141 attached to a hydraulic pump 144. If desired, the sample can be housed in a container that maintains the sample under an inert atmosphere such as nitrogen or argon.

In embodiments in which the irradiating is performed with electromagnetic radiation (e.g., as above), the electromagnetic radiation can have energy per photon of greater than $10^2$ eV, e.g., greater than $10^3$, $10^4$, $10^5$, $10^6$, or even greater than $10^7$ eV. In some embodiments, the electromagnetic radiation has an energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$, or even greater than $10^{21}$ hz. In some embodiments, the electromagnetic radiation has a frequency of between $10^{18}$ and $10^{22}$ hz, e.g., between $10^{19}$ to $10^{21}$ hz.

In some embodiments, a beam of electrons is used as the radiation source. Electron beams can be generated, e.g., by electrostatic generators, cascade generators, transformer generators, low energy accelerators with a scanning system, low energy accelerators with a linear cathode, linear accelerators, and/or pulsed accelerators. Electrons as an ionizing radiation source can be useful to crosslink outer portions of the substantially non-crosslinked polymeric material, e.g., inwardly from an outer surface of less than 0.5 inch, e.g., less than 0.4 inch, 0.3 inch, 0.2 inch, or less than 0.1 inch. In some embodiments, the energy of each electron of the electron beam is from about 0.3 MeV to about 10.0 MeV (million electron volts), e.g., from about 0.5 MeV to about 3.0 MeV, or from about 0.7 MeV to about 1.50 MeV.

In some embodiments, the irradiating (with any radiation source) is performed until the sample receives a dose of at least 0.25 Mrad, e.g., at least 1.0 Mrad, at least 2.5 Mrad, at least 5.0 Mrad, or at least 10.0 Mrad. In some embodiments, the irradiating is performed until the sample receives a dose of between 1.0 Mrad and 6.0 Mrad, e.g., between 1.5 Mrad and 4.0 Mrad.

In some embodiments, the irradiating is performed at a dose rate of between 5.0 and 1500.0 kilorads/hour, e.g., between 10.0 and 750.0 kilorads/hour, or between 50.0 and 350.0 kilorads/hours. Low rates can generally maintain the temperature of the sample, while high dose rates can cause heating of the sample.

In some embodiments, radical sources, e.g., azo materials, e.g., monomeric azo compounds such as 2,2'-azobis(N-cyclohexyl-2-methylpropionamide) (I), or polymeric azo materials such as those schematically represented by (II) in which the linking chains include polyethylene glycol units (N is, e.g., from about 2 to about 50,000), and/or polysiloxane units, peroxides, e.g., benzoyl peroxide, or persulfates, e.g., ammonium persulfate $(NH_4)_2S_2O_8$, are employed to crosslink the substantially non-crosslinked polymeric material.

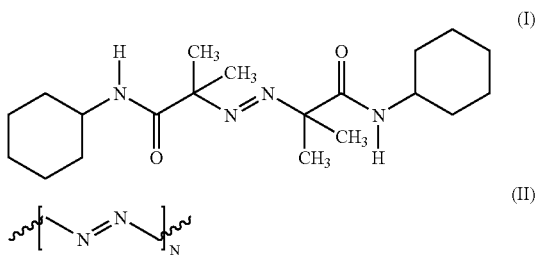

Azo materials are available from Wako Chemicals USA, Inc. of Richmond, Va.

Generally, to crosslink the substantially non-crosslinked polymeric material, the material is mixed, e.g., powder or melt mixed, with the radical source, e.g., using a roll mill, e.g., a Banbury® mixer or an extruder, e.g., a twin-screw extruder with counter-rotating screws. An example of a Banbury® mixer is the F-Series Banbury® mixer, manufactured by Farrel. An example of a twin-screw extruder is the WP ZSK 50 MEGAcompounder™, manufactured by Krupp Werner & Pfleiderer. Generally, the compounding or powder mixing is performed at the lowest possible temperature to prevent premature crosslinking. The sample is then formed into the desired shape, and further heated (optionally with application of pressure) to generate radicals in sufficient quantities to crosslink the sample.

Application of Pressure

After crosslinking, a pressure of greater than 10 MPa is applied to the crosslinked polymeric material, while heating the crosslinked material below a melting point of the crosslinked polymeric material at the applied pressure for a sufficient time to substantially reduce the reactive species trapped within the crosslinked polymeric material matrix, e.g., free radicals, radical cations, or reactive multiple bonds. Quenching such species produces an oxidation resistant crosslinked polymeric material. The high pressures, and temperatures employed also increase the crystallinity of the crosslinked polymeric material, which can, e.g., improve wear performance.

In some embodiments, the pressure applied is greater than 25 MPa, e.g., greater than 50 MPa, 75 MPa, 100 MPa, 150 MPa, 200 MPa, 250 MPa, 350 MPa, 500 MPa, 750 MPa, 1,000 MPa, or greater than 1,500 MPa. In some embodiments, the pressure is maintained for greater than 30 seconds, e.g., greater than 45 seconds, 60 seconds, 2.5 minutes, 5.0 minutes, 10 minutes, 20 minutes, 30 minutes, 60 minutes, greater than 90 minutes, or even greater than 120 minutes, before release of pressure back to nominal atmospheric pressure.

In some embodiments, prior to the application of any pressure above nominal atmospheric pressure, the crosslinked polymeric material is heated to a temperature that is between about 25° C. to about 0.5° C. below a melting point of the crosslinked polymeric material. This can enhance crystallinity of the crosslinked polymeric material prior to the application of any pressure.

In some embodiments, a pressure of above about 250 MPa is applied at a temperature of between about 100° C. to about 1° C. below a melting point of the crosslinked polymeric material at the applied pressure, and then the material is further heated above the temperature, but below a melting point of the crosslinked polymeric material at the applied pressure.

Manufacture of Preforms

Figure 4:
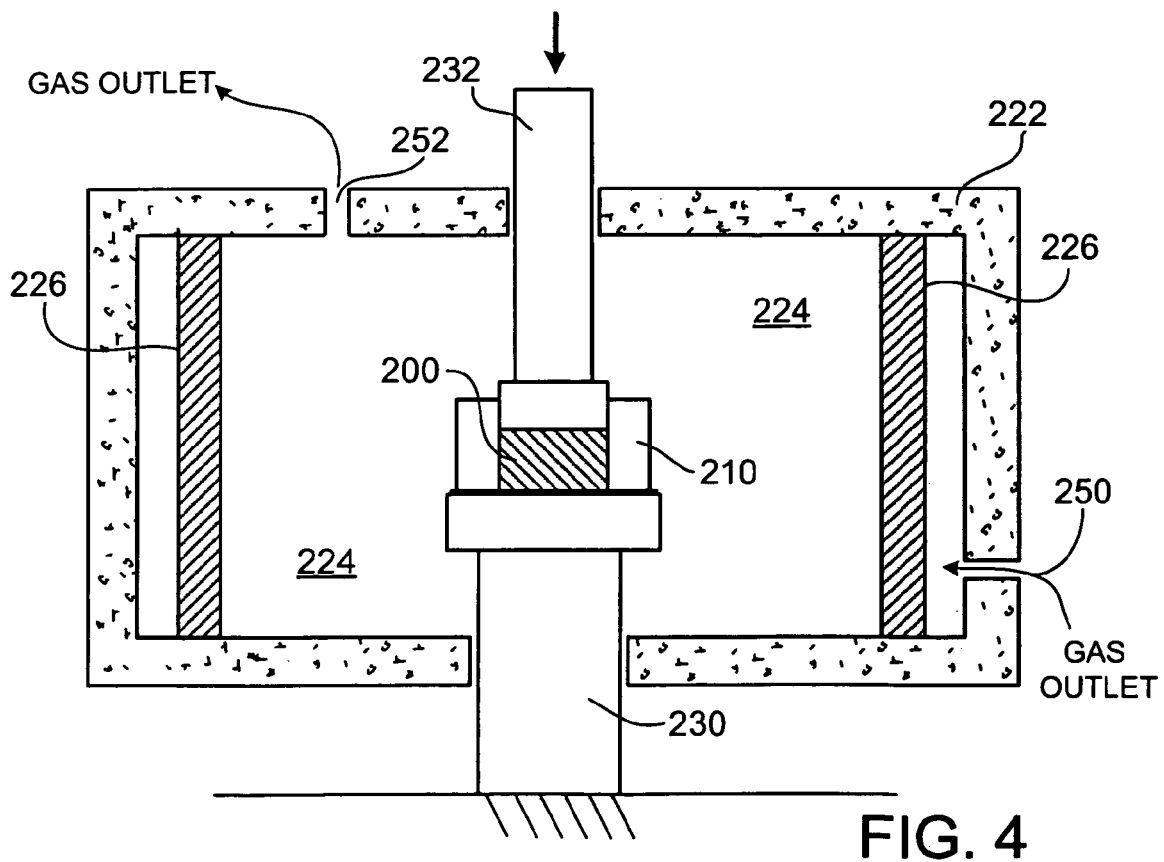
FIG. 4 is a cross-sectional view of a crosslinked UHMWPE rod in a mold disposed within a furnace.
Figure 5:
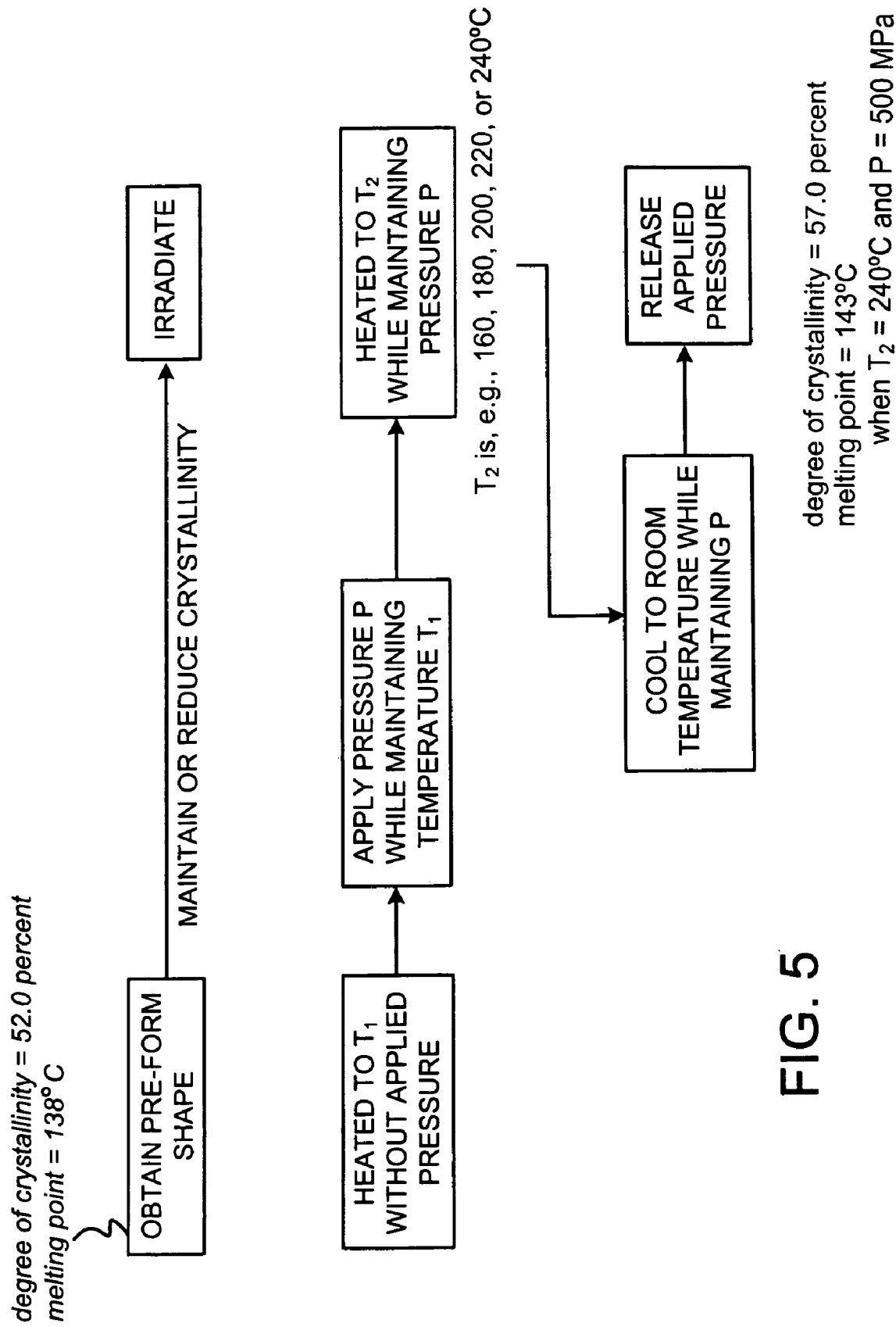
FIG. 5 is a block diagram, schematically illustrating methods of making oxidation resistant crosslinked UHMWPE.

Referring now to FIGS. 3-5, in particular embodiments, to make a crosslinked UHMWPE cylindrical preform that is resistant to oxidation, a substantially non-crosslinked cylindrical preform 200 is obtained, e.g., by machining rod stock to a desired height $H_1$ and desired diameter $D_1$. Preform 200 can be made from a substantially non-crosslinked UHMWPE having a melting point of around 138° C., and a degree of crystallinity of about 52.0 percent. This crystallinity is either reduced, e.g., by heating the preform 200 above the melting point of the UHMWPE, and then cooling, or the crystallinity is maintained, but not increased. Preform 200 is then subjected to gamma radiation, e.g., 50 kGr (5 Mrad; 1 Mrad=10 KGr) of gamma radiation, to crosslink the UHMWPE. After irradiation, the sample is press-fit into a pressure cell 210, and then the pressure cell 210 is placed into a furnace assembly 220. Furnace assembly 220 includes an insulated enclosure structure 222 that defines an interior cavity 224. Insulated enclosure structure 222 houses heating elements 224 and the pressure cell 210, e.g., that is made stainless steel, and that is positioned between a stationary pedestal 230 and a movable ram 232.

The crosslinked UHMWPE sample is first heated to a temperature $T_1$ below the melting point of the UHMWPE, e.g., 130° C., without the application of any pressure above nominal atmospheric pressure. After such heating, pressure P, e.g., 500 MPa of pressure, is applied to the sample, while maintaining the temperature $T_1$. Once pressurization has stabilized, the sample is further heated to a temperature $T_2$, e.g., 160, 180, 200, 220, or 240° C., while maintaining the pressure P. As noted, pressure is applied along a single axis by movable ram 232, as indicated by arrow 240. Pressure at the given temperature $T_2$ is generally applied for 10 minutes to 1 hour. During any heating, a gas such as an inert gas, e.g., nitrogen or argon, can be delivered to interior cavity 224 of insulated enclosure structure 222 through an inlet 250 that is defined in a wall of the enclosure structure 222. The gas exits through an outlet 252 that is defined in a wall of the enclosure structure, which maintains a pressure in the cavity 224 of about nominal atmospheric pressure. After heating to $T_2$ and maintaining the pressure P, the sample is allowed to cool to room temperature, while maintaining the pressure P, and then the pressure is finally released. The pressure cell 210 is removed from furnace 220, and then the oxidation resistant UHMWPE is removed from pressure cell 210.

Using the methods illustrated in FIGS. 3-5, by starting with an UHMWPE having a melting point of around 138° C., and a degree of crystallinity of about 52.0 percent, and using a temperature of $T_2$ of about 240° C., and a pressure P of about 500 MPa, one can obtain an oxidation resistant crosslinked UHMWPE that has a melting point greater than about 141° C., e.g., greater than 142, 143, 144, 145, or even greater than 146° C., and a degree of crystallinity of greater than about 52 percent, e.g., greater than 53, 54, 55, 56, 57, 58, 59, 60, 65, or even greater than 68 percent. In some embodiments, the crosslinked UHMWPE has a crosslink density of greater than about 100 mol/m³, e.g., greater than 200, 300, 400, 500, 750, or even greater than 1,000 mol/m³, and/or a molecular weight between crosslinks of less than about 9,000 g/mol, e.g., less than 8,000, 7,000, 6,000, 5,000, or even less than about 3,000 g/mol.

Measuring Crosslink Density

Crosslink density measurements are performed following the procedure outlined ASTM F2214-03. Briefly, rectangular pieces of the crosslinked UHMWPE are set in dental cement, and sliced into thin sections that are 2 mm thick. Small sections are cut out from these thin sections using a razor blade, giving test samples that are 2 mm thick by 2 mm wide by 2 mm high. A test sample is placed under a quartz probe of a dynamic mechanical analyzer (DMA), and an initial height of the sample is recorded. Then, the probe is immersed in o-xylene, heated to 130° C., and held at this temperature for 45 minutes. The UHMWPE sample is allowed to swell in the hot o-xylene until equilibrium is reached. The swell ratio $q_s$ for the sample is calculated using a ratio of a final height $H_f$ to an initial height $H_0$ according to formula (1):

$$q_s = [H_f/H_0]^3 \qquad (1).$$

The crosslink density $v_d$ is calculated from $q_s$, the Flory interaction parameter $\chi$ and the molar volume of the solvent $\Phi_1$ according to formula (2):

$$v_d = \frac{\ln(1 - q_s^{-1}) + q_s^{-1} + \chi q_s^{-2}}{\phi_1 (q_s^{-1/3} - q_s^{-1}/2)}, \qquad (2)$$

where $\chi$ is $0.33+0.55/qs$, and $\Phi_1$ is 136 cm$^3$/mol for UHMWPE in o-xylene at 130° C. Molecular weight between crosslinks $M_c$ can be calculated from $v_d$, and the specific volume of the polymer $v$ according to formula (3):

$$M_c = (v v_d)^{-1} \qquad (3).$$

Measurement of swelling, crosslink density and molecular weight between crosslinks is described in Muratoglu et al., *Biomaterials,* 20, 1463-1470 (1999).

Applications

The oxidation resistant crosslinked polymeric materials can be used in any application for which oxidation resistance, long-term stability, high wear resistance, low coefficient of friction, chemical/biological resistance, fatigue and crack propagation resistance, and/or enhanced creep resistance are desirable. For example, the oxidation resistant crosslinked polymeric materials are well suited for medical devices. For example, the oxidation resistant crosslinked polymeric material can be used as an acetabular liner, a finger joint component, an ankle joint component, an elbow joint component, a wrist joint component, a toe joint component, a hip replacement component, a tibial knee insert, an intervertebral disc, a heart valve, a stent, or part of a vascular graft.

Figure 6:
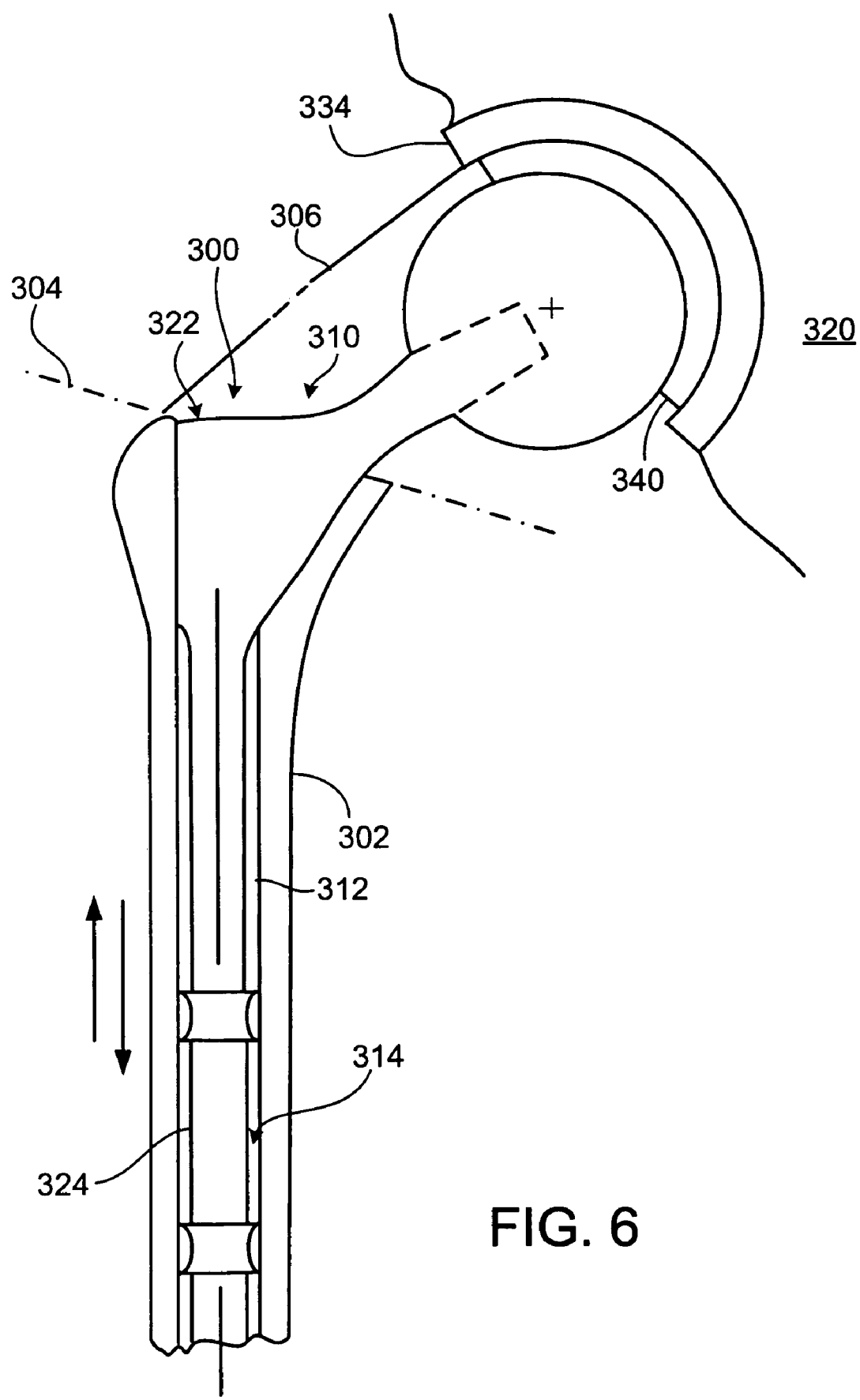
FIG. 6 is a partial cross-sectional view of a hip prosthesis having a bearing formed from crosslinked UHMWPE.

In a particular embodiment, the oxidation resistant crosslinked polymeric material is used as a liner in a hip replacement prostheses. Referring to FIG. 6, joint prosthesis 300, e.g., for treatment of osteoarthritis, is positioned in a femur 302, which has been resected along line 304, relieving the epiphysis 306 from the femur 302. Prosthesis 300 is implanted in the femur 302 by positioning the prosthesis in a cavity 310 formed in a portion of cancellous bone 312 within medullary canal 314 of the femur 302. Prosthesis 300 is utilized for articulating support between femur 302, and acetabulum 320. Prosthesis 300 includes a stem component 322, which includes a distal portion 324 disposed within cavity 310 of femur 302. Prosthesis 300 also includes a cup 334, which is connected to the acetabulum 320. A liner 340 is positioned between the cup 334 and the stem 322. Liner 44 is made of the oxidation resistant crosslinked polymeric material described herein.

EXAMPLES

The invention is further described in the following examples, which do not limit the scope of the invention described in the claims.

Materials and Apparatuses

Non-crosslinked, ram-extruded rod stock of GUR 1050 UHMWPE (Hoechst-Ticona, Bayport, Tex.) was purchased from PolyHi Solidur of Fort Wayne, Ind. The non-crosslinked rod stock was machined into cylinders that were 25 mm in length and 12.5 mm in diameter. Tolerances were held in the machining such that the cylinders can be pressed fitted into a hollow, cylindrical high-pressure cell using human manipulation. The high pressure cell is made from D2 tool alloy, and is heated by direct contact with heating elements. The UHMWPE sample is pressed by sandwiching the sample between plates of polytetrafluoroethylene and copper, with the polytetrafluoroethylene plates being in direct contact with the UHMWPE sample. After machining, the UHMWPE cylindrical preforms were subjected to 50 kGy (5 Mrad) of gamma radiation in air using Sterix Isomedix's, Northborough, Mass. facility. The crosslinked UHMWPE preforms were stored in water to minimize additional exposure to ambient air. Pressure was applied to the crosslinked samples using a CARVER® Model 3912 eleven ton, four column manual hydraulic press. Samples were sectioned using a Leitz Wetzlar (Leica, Nussloch, Germany) sledge microtome.

Accelerated aging of UHMWPE samples was performed using a Parr® 6300 series oxygen bomb reactor filled with oxygen gas to a pressure of 5 atmospheres. The bomb reactor was heated to 70° C. temperature, and held at this temperature for a period of two weeks to completely oxidize the samples (see ASTM F2003-02).

Oxidation index (OI) was determined for each sample using a Nicolet Magna 860 FTIR spectrometer. Thin sections that were 100-200 μm thick were provided by the microtome. A sample size of six was used to calculate the average oxidation index.

Figure 7:
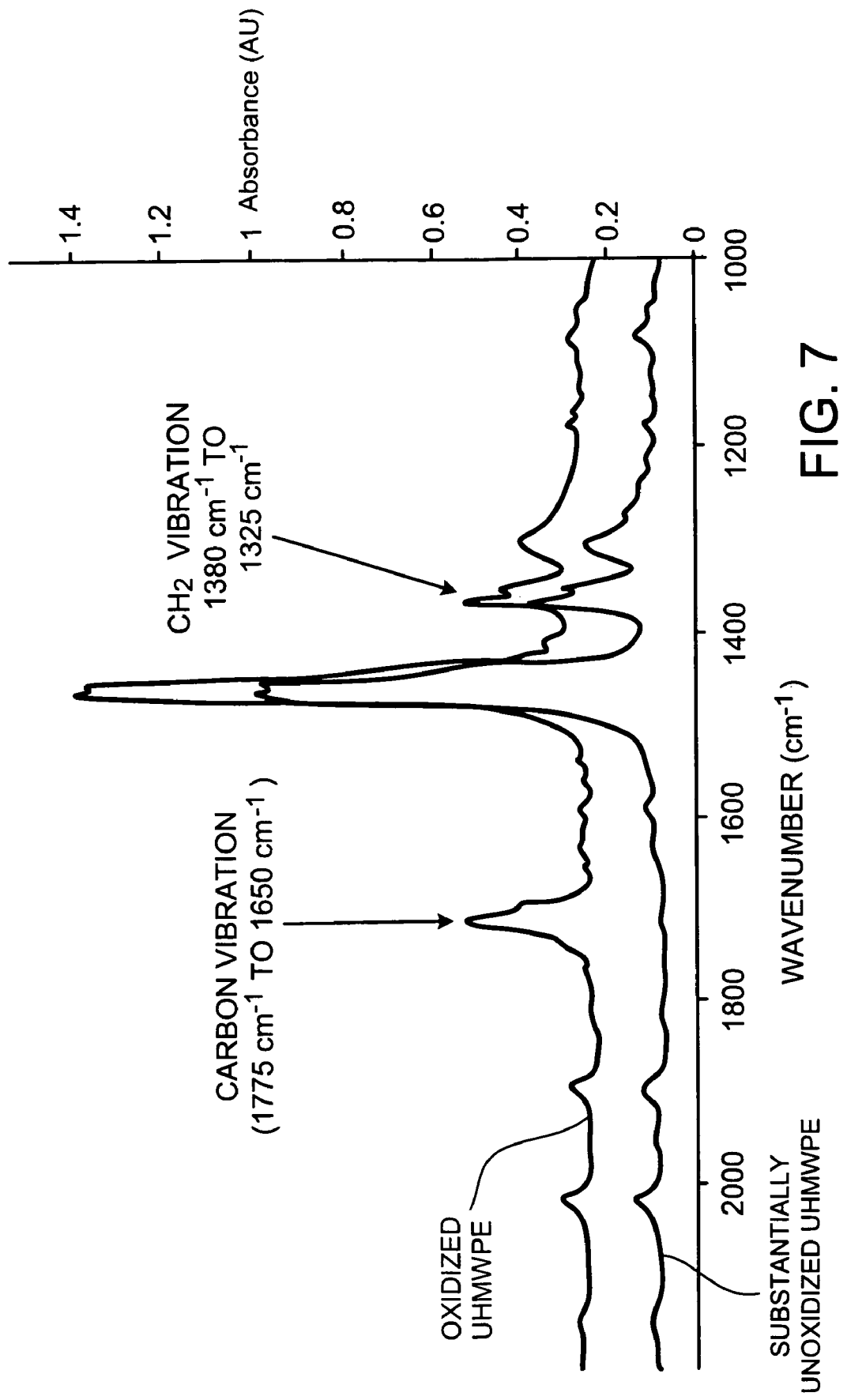
FIG. 7 is a Fourier transform (FT) infrared spectrum of oxidized, and substantially unoxidized UHMWPE.
Figure 7B:
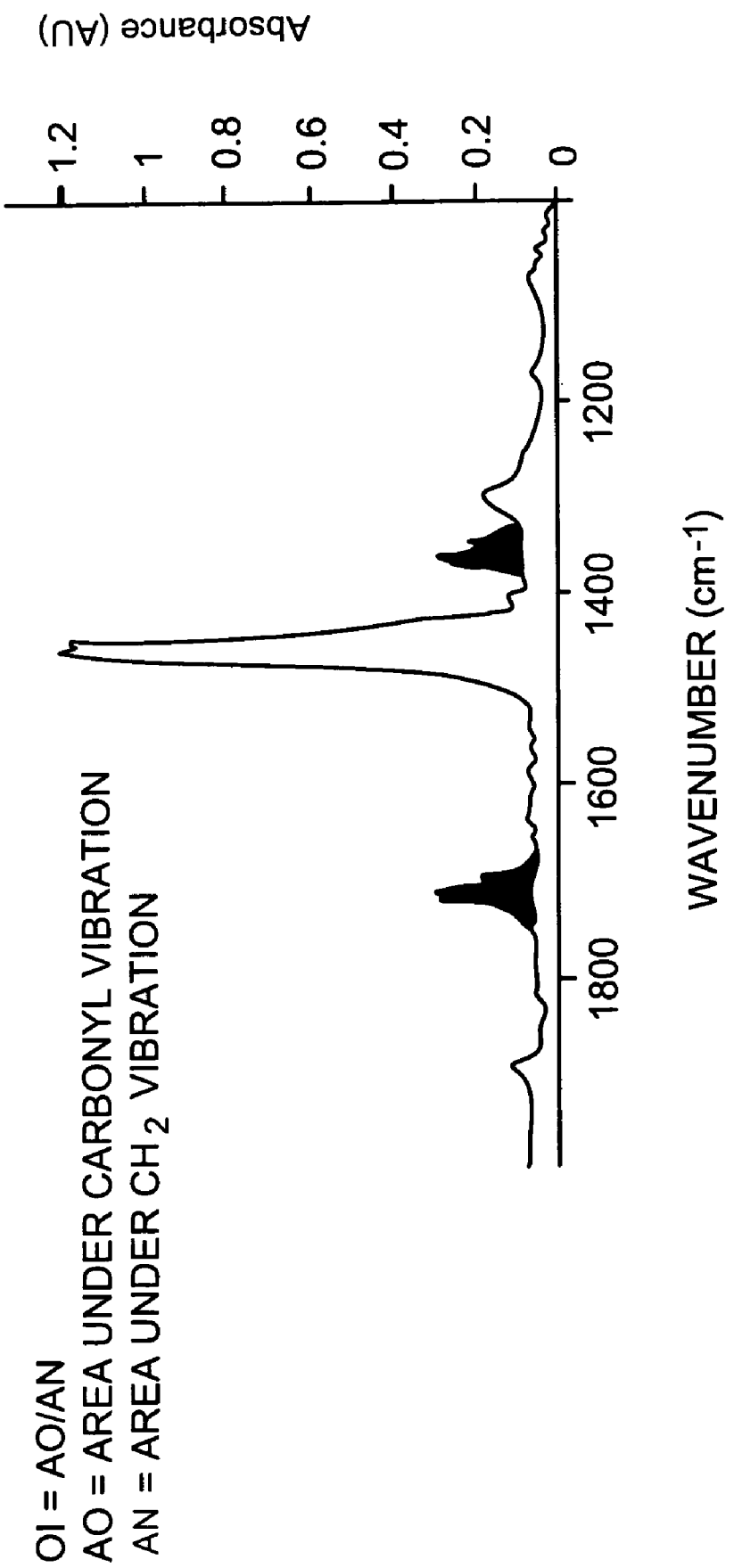
FIG. 7B is an FTIR spectrum of oxidized UHMWPE, illustrating calculation of oxidation index (OI).

Referring to FIG. 7, substantially unoxidized UHMWPE does not exhibit a substantial carbonyl vibration in the 1650 to 1775 cm$^{-1}$ region, while oxidized UHMWPE does exhibit a substantial vibration in that region due to carbonyl groups in the oxidized UHMWPE (e.g., of aldehyde, ketone and/or acid groups). As FIG. 7 shows, both oxidized and substantially unoxidized UHMWPE exhibit a strong methylene (CH$_2$) vibration in the 1325 to 1380 cm$^{-1}$ region. Referring now to FIG. 7A, the oxidation index OI of an oxidized sample is the ratio of the area under the spectrum in the carbonyl region (AO) to the area under the spectrum in the methylene vibration region (AN).

Pressure Application Protocols

The following experimental groups were evaluated.

(1) Pressure of 100, 200, 300, 400 and 500 MPa was applied to irradiated UHMWPE cylindrical specimens at room temperature for a period of 20 minutes, followed by pressure release.

(2) Irradiated UHMWPE cylindrical specimens were heated to 130° C., and then a pressure of either 100, 300, or 500 MPa was applied to the sample for 20 minutes. Each sample was allowed to slow cool to room temperature, and then once at room temperature, the pressure was released.

(3) Irradiated UHMWPE cylindrical specimens were heated to 130° C. without the application of pressure above nominal atmospheric pressure. After such heating, a pressure of 500 MPa was applied to the sample, while maintaining 130° C. Once pressurization had stabilized, the sample was further heated to a temperature of either 160, 180, 200, 220, or 240° C., while maintaining the 500 MPa pressure applied to the sample. Pressure at the given temperature was applied for 20 minutes. Each sample was then allowed to slowly cool to room temperature, and then once at room temperature, the pressure was released. In these particular examples, the cooling rate was between about 40 and 100° C./hour.

Results and Discussion

FTIR experiments showed irradiated UHMWPE samples that were bomb aged exhibited a maximum oxidation index of 1.68+/−0.13, in comparison to 0.29+/−0.09 for the air aged UHMWPE. Therefore, 0.29 was subtracted from the OI of the samples to accurately reflect oxidation indexes solely associated with the bomb aging.

Figure 8:
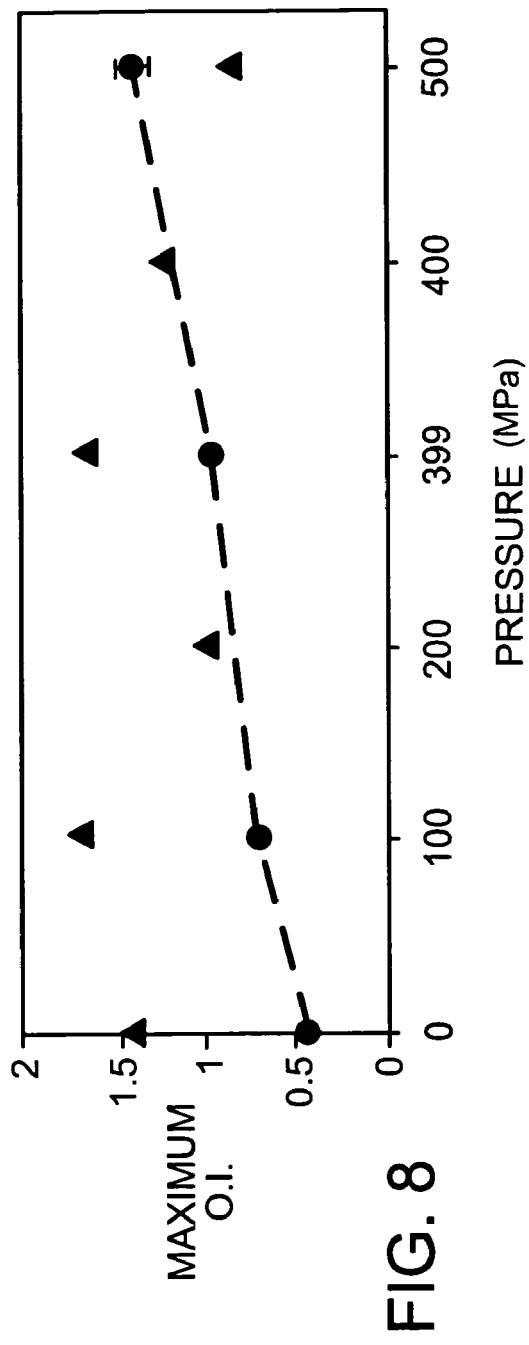
FIG. 8 is a plot of maximum oxidation index of irradiated UHMWPE versus pressure at room temperature (triangles), and at 130° C. (solid circles connected by dotted line).

FIG. 8 shows no general trend in the oxidation index OI for experimental group (1) after accelerated ageing (triangles). However, referring to FIG. 8, the oxidation index OI for experimental group (2) after accelerated aging shows a clear increase in the OI with increasing pressure (solid circles connected by dashed line).

Figure 9:
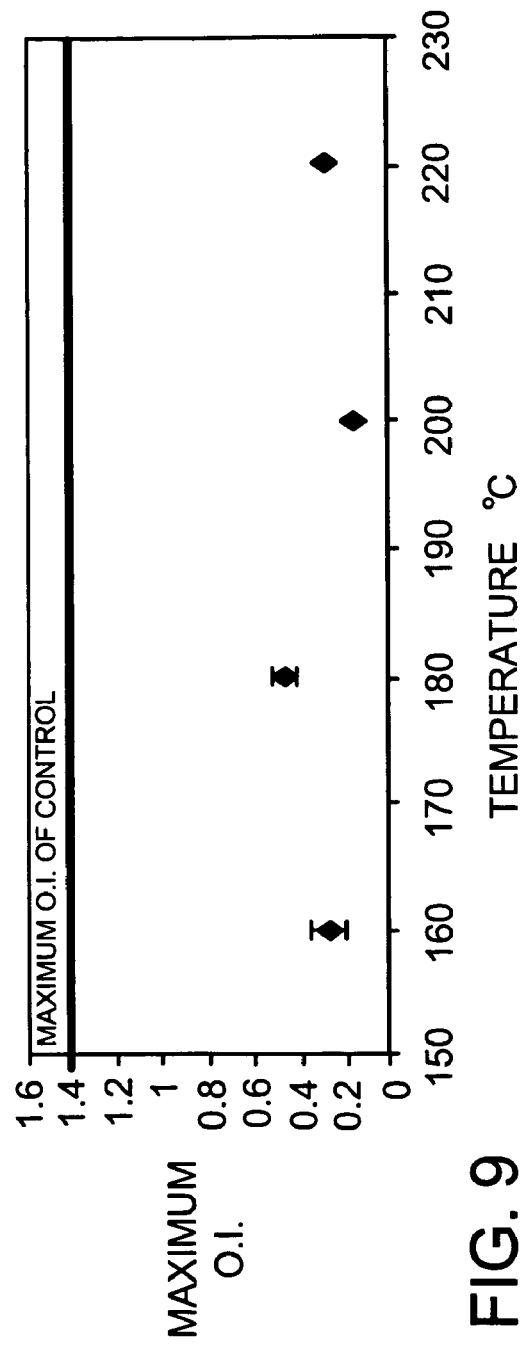
FIG. 9 is a plot of maximum oxidation index of irradiated UHMWPE versus temperature for heating in the range of 160-220° C. (solid line is control).

FIG. 9 shows that for experimental group (3) after accelerated ageing, the OI decreased substantially for each member of the group, but there appeared to be no apparent trend in the OI as a function of annealing temperatures.

From the above-noted results, it appears that (a) application of high pressure alone does not affect resistance to oxidation; (b) high pressure annealing increases oxidation with increasing pressure at 130° C.; and (c) high pressure annealing at temperatures in the range of about 160-220° C. substantially decreases oxidation at an applied pressure of 500 Mpa.

Figure 10:
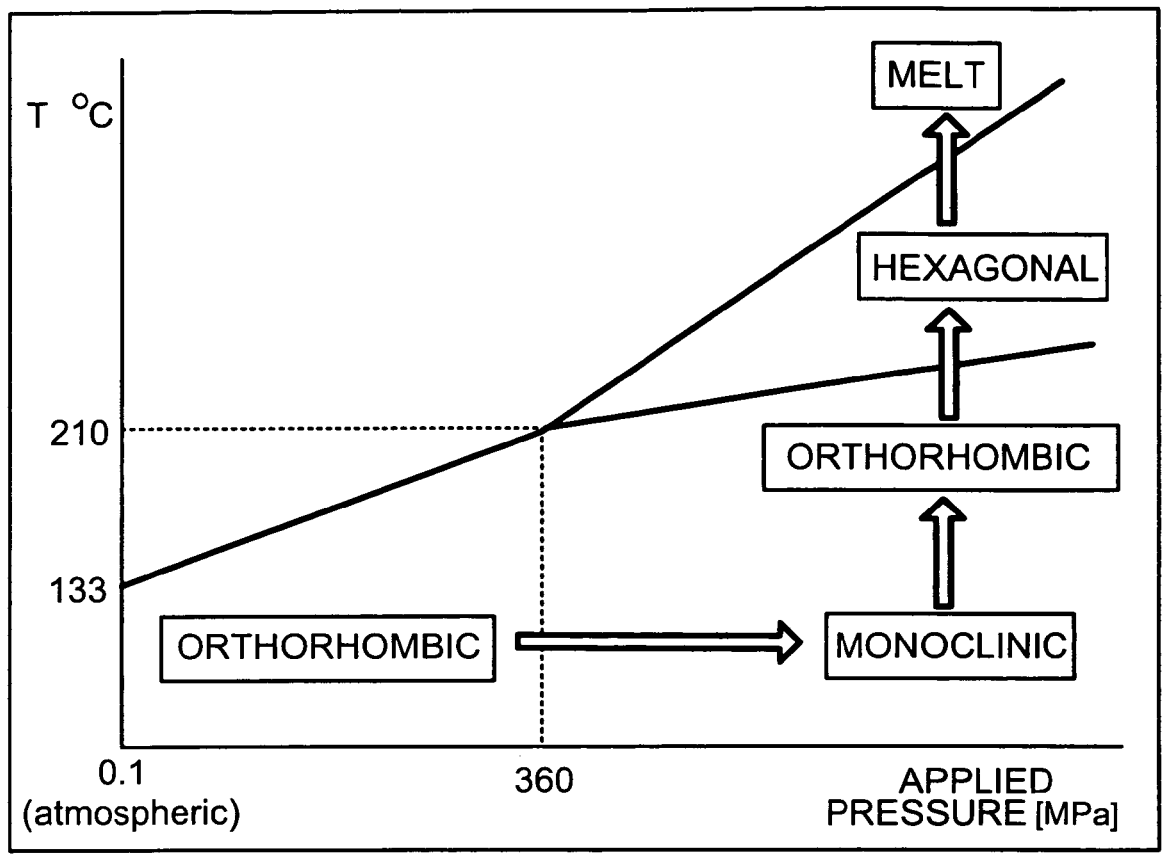
FIG. 10 is a phase diagram for UHMWPE, showing temperatures and pressures when the UHMWPE is in the melt, along with its crystalline structure.

It is believed that these results can be explained with the help of the phase diagram for polyethylene. FIG. 10 shows that the melting temperature of polyethylene increases approximately 20° C. per 100 MPa of applied pressure from an initial value of 133° C. at atmospheric pressure. In experimental group (1), there was insufficient thermal energy at high pressures to decrease free radical concentrations. In experimental group (2), the annealing temperature of 130° C. was much lower than melting point at 500 MPa (approximately 233° C.), 300 MPa (about 193° C.), or 100 MPa (153° C.). Consequently, the OI increased with increasing pressure at isothermal annealing conditions. For experimental group (3), the annealing temperature range of 160-220° C. is still below the estimated melting point of 233° C. at 500 MPa, but the high thermal energy was enough to substantially reduce the free radical load of the samples. In addition, the polyethylene chains in the hexagonal regime of the phase diagram associated with those samples of experimental group (3) have increased mobility, which is desirable for quenching any reactive species, leading to lower oxidation indexes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of making an oxidation resistant crosslinked polymeric material, the method comprising:
   obtaining a substantially non-crosslinked polymeric material having a first degree of crystallinity;
   maintaining or reducing the first degree of crystallinity of the substantially non-crosslinked polymeric material;
   crosslinking the substantially non-crosslinked polymeric material, to provide a crosslinked polymeric material; and then
   applying a pressure of greater than 10 MPa to the crosslinked polymeric material, while heating the crosslinked material to a temperature below a melting point of the crosslinked polymeric material at the applied pressure for a time sufficient to provide an oxidation resistant crosslinked polymeric material;
   wherein the crosslinking occurs below a melting point of the substantially non-crosslinked polymeric material.

2. The method of claim 1, further comprising, prior to the application of pressure above nominal atmospheric pressure, heating the crosslinked polymeric material to a temperature that is between about 25° C. to about 0.5° C. below a melting point of the crosslinked polymeric material.

3. The method of claim 1, wherein applying pressure while heating includes applying a pressure of above about 250 MPa at a temperature of between about 100° C. to about 1° C. below a melting point of the crosslinked polymeric material at the applied pressure, and then further heating above the temperature, but below a melting point of the crosslinked polymeric material at the applied pressure.

4. The method of claim 1, further comprising, prior to crosslinking, heating the substantially non-crosslinked polymeric material having the first degree of crystallinity above a melting point of the substantially non-crosslinked polymeric material, at the applied pressure.

5. The method of claim 4, wherein the substantially non-crosslinked polymeric material is ultra-high molecular weight polyethylene (UHMWPE), wherein the first degree of crystallinity is between about 50 and about 55 percent, and wherein a degree of crystallinity of the UHMWPE after cooling the melted UHMWPE to about 25° C. is between about 32 percent and about 48 percent.

6. The method of claim 1, further comprising, prior to crosslinking, heating the substantially non-crosslinked polymeric material having the first degree of crystallinity above a melting point of the substantially non-crosslinked polymeric material, and then cooling the substantially non-crosslinked polymeric material with a fluid having a temperature below about 0° C.

7. The method of claim 1, wherein applying pressure while heating includes heating above about 100° C.

8. The method of claim 1, wherein the non-crosslinked polymeric material is substantially-free of biologically leachable additives.

9. The method of claim 1, wherein the crosslinking step comprises irradiating the substantially non-crosslinked polymeric material with an ionizing radiation.

10. The method of claim 9, wherein the ionizing radiation is in the form of gamma radiation.

11. The method of claim 9, wherein the ionizing radiation is applied at a total dose of greater than 1 Mrad.

12. The method of claim 9, wherein the ionizing radiation is applied at a dose rate of greater than 0.1 Mrad/hour.

13. The method of claim 1, wherein the substantially non-crosslinked polymeric material comprises ultra-high molecular weight polyethylene.

14. The method of claim 1, wherein the substantially non-crosslinked polymeric material comprises a melt processible polymer or a blend of polymers.

15. The method of claim 1, wherein the oxidation resistant crosslinked polymeric material is in the form of a cylindrical rod.

16. The method of claim 1, wherein pressure is applied along a single axis.

17. The method of claim 1, wherein the applied pressure is greater than 350 MPa.

18. The method of claim 1, wherein the time is greater than 45 seconds.

19. The method of claim 1, wherein the crosslinking occurs at about nominal atmospheric pressure.

20. The method of claim 1, wherein the substantially non-crosslinked polymeric material is an olefin or a mixture of olefins.

21. A medical endoprosthesis, or portion thereof, comprising an oxidation resistant crosslinked polymeric material made by the method of claim 1.

22. A crosslinked ultra-high molecular weight polyethylene having a melting point greater than about 141° C., a maximum oxidation index greater than 0, and a degree of crystallinity of greater than about 52 percent.

23. The crosslinked ultra-high molecular weight polyethylene of claim 22, wherein the degree of crystallinity is greater than about 56 percent.

24. The crosslinked ultra-high molecular weight polyethylene (UHMWPE) of claim 22, having a crosslink density of greater than about 100 mol/m3.

25. The crosslinked ultra-high molecular weight polyethylene (UHMWPE) of claim 22, having a molecular weight between crosslinks of less than about 9,000 g/mol.

26. A medical device comprising the crosslinked ultra-high molecular weight polyethylene (UHMWPE) of claim 22.

27. A preform shape comprising the crosslinked ultra-high molecular weight polyethylene (UHMWPE) of claim 22.

28. A method of making an oxidation resistant preform, the method comprising:
   obtaining a preform comprising a substantially non-crosslinked polymeric material having a first degree of crystallinity;
   maintaining or reducing the first degree of crystallinity of the substantially non-crosslinked polymeric material;
   crosslinking the substantially non-crosslinked polymeric material, to provide a preform comprising a crosslinked polymeric material; and then
   applying a pressure of greater than 10 MPa to the preform comprising the crosslinked polymeric material, while heating the crosslinked material to a temperature below a melting point of the crosslinked polymeric material at the applied pressure for a time sufficient to provide an oxidation resistant preform;
   wherein the crosslinking occurs below a melting point of the substantially non-crosslinked polymeric material.

29. The method of claim 28, wherein the preform comprising the substantially non-crosslinked polymeric material is in the form of a cylindrical rod.

30. The method of claim 28, wherein the preform is obtained by extrusion.

31. The method of claim 1, wherein applying pressure while heating includes applying the pressure at an elevated temperature of between about 100° C. to about 1° C. below a melting point of the crosslinked polymeric material at the applied pressure.

32. The method of claim 31, wherein applying pressure while heating includes applying a pressure of above about 50 MPa.

33. The crosslinked ultra-high molecular weight polyethylene of claim 22, where the crosslinked ultra-high molecular weight polyethylene (UHMWPE) is produced by a process including the step of applying a pressure of greater than 10 MPa to the UHMWPE while heating the crosslinked UHMWPE to a temperature below a melting point of the crosslinked UHMWPE for a sufficient time to reduce the reactive species within the crosslinked UHMWPE polymer matrix.

34. A method of making an oxidation resistant crosslinked polymeric material, the method comprising:
   obtaining a substantially non-crosslinked polymeric material having a first degree of crystallinity;
   maintaining or reducing the first degree of crystallinity of the substantially non-crosslinked polymeric material;
   crosslinking the substantially non-crosslinked polymeric material below a melting point of the substantially non-crosslinked polymeric material, to provide a crosslinked polymeric material; and then
   applying a pressure to reduce the reactive species within the crosslinked polymeric material while heating the crosslinked material to a temperature below a melting point of the crosslinked polymeric material at the applied pressure for a time sufficient to provide an oxidation resistant crosslinked polymeric material, the reactive species being from the group consisting of free radicals, radical cations, and reactive double bonds.

35. The method of claim 34, where the reactive species are free radicals.

36. The method of claim 34, wherein applying pressure while heating includes applying a pressure of above about 50 MPa at a temperature of between about 100° C. to about 1° C. below a melting point of the crosslinked polymeric material at the applied pressure, and then further heating above the temperature, but below a melting point of the crosslinked polymeric material at the applied pressure.

37. The method of claim 36, wherein applying pressure while heating includes applying a pressure of above about 100 MPa.

38. A method of making an oxidation resistant crosslinked polymeric material, the method comprising:
   obtaining a substantially non-crosslinked polymeric material having a first degree of crystallinity;
   maintaining or reducing the first degree of crystallinity of the substantially non-crosslinked polymeric material;
   crosslinking the substantially non-crosslinked polymeric material, to provide a crosslinked polymeric material; and then
   applying a pressure of greater than about 25 MPa to the crosslinked polymeric material, while heating the crosslinked material to a temperature of between about 100° C. to about 1° C. below a melting point of the crosslinked polymeric material at the applied pressure, and then further heating above the temperature, but below a melting point of the crosslinked polymeric material at the applied pressure.

39. The method of claim 38, wherein a pressure of greater than about 250 MPa is applied to the crosslinked polymeric material while heating the crosslinked material.

* * * * *

UNITED STATES PATENT AND TRADEMARK OFFICE
CERTIFICATE OF CORRECTION

| | | |
|---|---|---|
| PATENT NO. | : 7,635,725 B2 | Page 1 of 1 |
| APPLICATION NO. | : 11/359845 | |
| DATED | : December 22, 2009 | |
| INVENTOR(S) | : Bellare et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 834 days.

Signed and Sealed this

Ninth Day of November, 2010

David J. Kappos
*Director of the United States Patent and Trademark Office*